(12) United States Patent
Yamashiro et al.

(10) Patent No.: US 8,460,926 B2
(45) Date of Patent: Jun. 11, 2013

(54) AQUEOUS SOLUTION FOR CELL PRESERVATION

(75) Inventors: Naoto Yamashiro, Fukushima (JP); Kohichi Saze, Fukushima (JP); Osamu Ohneda, Ibaraki (JP); Masumi Nagano, Ibaraki (JP)

(73) Assignee: Nippon Zenyaku Kogyo Co., Ltd, Koriyama-Shi, Fukushima (JP)

( * ) Notice: Subject to any disclaimer, the term of this patent is extended or adjusted under 35 U.S.C. 154(b) by 1346 days.

(21) Appl. No.: 12/084,655

(22) PCT Filed: Nov. 17, 2006

(86) PCT No.: PCT/JP2006/322985
§ 371 (c)(1),
(2), (4) Date: Jul. 21, 2008

(87) PCT Pub. No.: WO2007/058308
PCT Pub. Date: May 24, 2007

(65) Prior Publication Data
US 2009/0142830 A1    Jun. 4, 2009

(30) Foreign Application Priority Data

Nov. 17, 2005    (JP) .................................. 2005-333203

(51) Int. Cl.
*C12N 5/071* (2010.01)
*C12N 5/00* (2006.01)

(52) U.S. Cl.
USPC .......................................... 435/366; 435/374

(58) Field of Classification Search
USPC .................................. 435/366, 374
See application file for complete search history.

(56) References Cited

U.S. PATENT DOCUMENTS

| 6,680,305 B1 | 1/2004 | Segall |
| 2002/0068360 A1 | 6/2002 | Brockbank et al. |
| 2003/0035843 A1 | 2/2003 | Livesey |
| 2003/0118982 A1* | 6/2003 | Yamamoto et al. ............ 435/1.3 |
| 2007/0042341 A1* | 2/2007 | Xu et al. ............................ 435/2 |
| 2009/0197331 A1* | 8/2009 | Kato et al. ..................... 435/374 |

FOREIGN PATENT DOCUMENTS

| JP | 63 216476 A | 9/1988 |
| JP | 06-46840 A | 2/1994 |
| JP | 11-292701 A | 10/1999 |
| JP | 2001-247401 A | 9/2001 |
| JP | 2003-505024 A | 2/2003 |
| JP | 2003-530406 A | 10/2003 |
| WO | WO 91/17655 A1 | 11/1991 |
| WO | WO 92/14360 A1 | 9/1992 |
| WO | WO-01/05941 A2 | 1/2001 |

OTHER PUBLICATIONS

Sasaki et al. (Development of a novel serum-free freezing medium for mammalian cells using the silk protein sericin. Biotechnol. Appl. Biochem Oct. 2005 42, 183-188).*
Karlson et al. (A Cold-regulated Nucleic Acid-binding Protein of Winter Wheat Shares a Domain with Bacterial Cold Shock Protein. J. of Biological Chemistry 277(38):35248-35256).*
Chinese Office Action issued on Jun. 30, 2010 in Chinese Application No. 2006/800429805.
Xiang, et al. "Study on Cryopreservation technology of Chlamydomonas Cells by Vitrification", Chinese Journal of Cell Biology, vol. 13, No. 2, Dec. 31, 2001, pp. 110-113.
Japanese Office Action issued in corresponding JP Appl. No. 2007-545317 on Jun. 14, 2012.
European Search Report issued in corresponding European Application No. 06832864.0 on Mar. 46, 2013.

* cited by examiner

*Primary Examiner* — Karen Cochrane Carlson
*Assistant Examiner* — Natalie Moss
(74) *Attorney, Agent, or Firm* — Birch Stewart Kolasch Birch LLP (57) ABSTRACT

To provide an aqueous solution for cell preservation which is free of a natural animal-derived component such as a basal medium or serum. An aqueous preservation solution showing a high cell survival rate was obtained by removing a natural animal-derived component such as a basal medium or serum and controlling other components and their concentrations.

20 Claims, 4 Drawing Sheets

[Fig. 2a]

No induction
(aqueous solution for cell preservation I)

Aqueous solution for cell preservation M

Aqueous solution for cell preservation I

Aqueous solution for cell preservation K

Scale bar = 200 μm

[Fig. 2b]

No induction
(aqueous solution for cell preservation I)

Aqueous solution for cell preservation M

Aqueous solution for cell preservation I

Aqueous solution for cell preservation K

Scale bar = 20 μm

US 8,460,926 B2

AQUEOUS SOLUTION FOR CELL PRESERVATION

TECHNICAL FIELD

The present invention relates to an aqueous solution for cell preservation capable of preserving cells for a long term by a simple operation, and more specifically, to an aqueous solution for cell preservation free of natural animal-derived component such as a basal medium or serum.

BACKGROUND ART

Conventionally, cryopreservation has been performed for preventing cultured cells from cell deterioration with successive passages and contamination by germs so that the cells can be utilized for a long term. Known as such a general method for cell preservation is a method of preserving cells in liquid nitrogen (−196° C.) by: suspending the cells in a culture medium containing dimethyl sulfoxide (hereinafter, referred to as DMSO) and serum; dispensing the suspension in a cryotube or an ampule; and cooling the suspension with a program freezer.

Various compositions of preservation solutions for cryopreservation have been prepared depending on the types of cells to be preserved. For example, a serum-free culture medium for cryopreservation has been developed for cultured cells to be cultured in a serum-free culture medium (see, for example, Patent Document 1). In addition, a solution for cryopreservation varies in quality because of different serum lots. In addition, essentially unnecessary components for the preservation of cells, such as various kinds of cytokines, growth factors, and hormones contained in serum may change the property of the preserved cells, so solutions for cryopreservation using no serum have been developed (see, for example, Patent Document 2).

However, the serum-free cryopreservation solution disclosed in Patent Document 1 includes a basal medium containing a variety of components. For example, an RPMI1640 culture medium contains a large number of origin undefined amino acids. The influence of those culture medium components on the preserved cells is also unknown. In addition, purified albumin is used in Patent Document 2. However, it might be contaminated by various components depending on the degree of refinement of the albumin, so problems concerning influences on cells remain.

Considering the potential influences on cells to be preserved in solution containing serum or basal medium, especially for medical use, development of a chemically well-defined cell preservation solution free of natural animal-derived components is desired. Such a cell preservation solution includes origin-defined components, and thus, it can be expected to have an advantage that the quality of the solution is kept constant.

Unfortunately, conventional cell preservation solution needs basal medium, serum or serum replacement, such as serum albumins, purified albumins and the like to perform long-term and stable cell preservation. Therefore, a cell preservation solution that is totally free of natural animal-derived component has not been obtained yet Patent Document 1: JP 63-216476 A
Patent Document 2: JP 2002-233356 A

DISCLOSURE OF THE INVENTION

Problem to be Solved by the Invention

It is an object of the present invention to provide an aqueous solution for cell preservation free of natural animal-derived component such as a basal medium or serum. Another object of the present invention is to provide a method for cell preservation using the aqueous preservation solution.

Means for Solving the Problems

As a result of intensive studies for solving the above problems, the inventors of the present invention have finally completed the present invention by finding out an aqueous preservation solution that allows cells after preservation to show a high survival rate by adjusting other components and their concentrations excluding any natural animal-derived component such as a basal medium or serum. Furthermore, the inventors have completed a method for cell preservation by preparing cells with the aqueous preservation solution of the present invention.

The present invention relates to a method for cell preservation using an aqueous solution for cell preservation according to any one of the following items (1) to (17):

(1) an aqueous solution for cell preservation containing: a thickener, a cryoprotectant, and sugars, and free of natural animal-derived components;

(2) an aqueous solution for cell preservation according to the above item (1), further containing: a pH adjuster;

(3) an aqueous solution for cell preservation according to the above item (1) or (2), in which the natural animal-derived components are serum and a component derived from basal medium.

(4) an aqueous solution for cell preservation containing the following compositions (a) to (e) and having a pH of 6.5 to 9.0:

(a) 1.0 to 20.0 w/v % of a cryoprotectant;
(b) 1.0 to 10.0 w/v % of sugars;
(c) 0.1 to 1.0 w/v % of a thickener;
(d) 0.01 to 1.0 w/v % of a pH adjuster; and
(e) a proper amount of water;

(5) an aqueous solution for cell preservation according to any one of the above items (1) to (4), in which an osmotic pressure is 1,000 mOsm or more;

(6) an aqueous solution for cell preservation according to the above item (5), in which the osmotic pressure is 1,000 to 2,700 mOsm;

(7) an aqueous solution for cell preservation according to any one of the items (1) to (6), in which the thickener is carboxymethylcellulose (CMC), sodium carboxymethylcellulose (CMC-Na), or an organic acid polymer;

(8) an aqueous solution for cell preservation according to the above items (7), in which the organic acid polymer is sodium polyacrylate;

(9) an aqueous solution for cell preservation according to any one of the above items (1) to (8), in which the cryoprotectant is dimethyl sulfoxide (DMSO) or propylene glycol;

(10) an aqueous solution for cell preservation according to any one of the above items (1) to (9), in which the sugar is glucose;

(11) an aqueous solution for cell preservation according to any one of the above items (1) to (10), in which the pH adjuster is a phosphate buffer;

(12) an aqueous solution for cell preservation containing the following compositions (a) to (e) and having a pH of 6.5 to 9.0:
 (a) 5.0 to 12.0 w/v % of DMSO;
 (b) 3.0 to 5.0 w/v % of glucose;
 (c) 0.2 to 0.7 w/v % of a thickener;
 (d) 0.01 to 1.0 w/v % of a phosphate buffer; and
 (e) a proper amount of water;

(13) an aqueous solution for cell preservation according to any one of the above items (1) to (12), in which cells to be preserved are any of lymphocytes, spleen cells, thymocytes, animal cells, somatic stem cells, and embryonic stem cells;

(14) an aqueous solution for cell preservation according to any one of the above items (1) to (13), the solution being used for medical applications;

(15) an aqueous solution for cell preservation according to any one of the above items (1) to (14), in which the method for cell preservation is cryopreservation;

(16) an aqueous solution for cell preservation according to any one of the above items (1) to (15), in which the survival rate of cells after the preservation is at least 80%;

(17) an aqueous solution for cell preservation according to any one of the above items (1) to (15), in which the proliferation ability of cells is retained after preservation for 4 days at $-80°$ C. and then 72 days at $-196°$ C.; and (18) an aqueous solution for cell preservation according to any one of the above items (1) to (15), in which the differentiation ability of cells after preservation is retained.

(19) a method for cell preservation including: dispersing cells in the aqueous solution for cell preservation according to any one of the above items (1) to (15); dispensing the cells into containers; and subjecting the cells to cryopreservation; or (20) a method for cell preservation according to the above item (19), in which the number of the dispensed cells is $1\times10^5$ to $1\times10^7$ cells/mL.

Effects of the Invention

The aqueous solution for cell preservation established by the present invention is free of natural animal-derived component such as a basal medium or serum, so that it can be safely used for medical applications because of its low possibility of being contaminated with impurities for preserved cells such as bovine leukemia virus, prion and the like. In addition, a preservation method using the aqueous solution for cell preservation of the present invention is able to provide a high cell survival rate and/or retain the proliferation potential and differentiation ability of cells. Furthermore, cells can be presented at a low cost, because the solution is free of origin-undefined components, for example, basal medium, serum and the like.

BEST MODE FOR CARRYING OUT THE INVENTION

An aqueous solution for cell preservation of the present invention refers to an aqueous solution that contains a thickener, a cryoprotectant, and sugars while being free of any natural animal-derived component to preserve cells. Further, the solution refers to an aqueous solution that contains a pH adjuster but is free of any natural animal-derived component. This is because the influence of the natural animal-derived component on cells to be preserved is unknown. The characteristic feature of the aqueous solution for cell preservation of the present invention is that the composition of the solution includes only origin well-defined components that do not affect the cells to be preserved. Thus, it is desirable that no natural animal-derived component be included in the solution irrespective of a combination of the natural animal-derived components.

Natural animal-derived components, which are not desirably included in the aqueous solution for cell preservation of the present invention, include natural animal-derived component conventionally used for the preservation and culture of cells and other natural animal-derived component. For example, serum, basal medium of origin-undefined and the like which can be used for cell culture are included. Further, purified albumin, purified protein, chicken egg yolk, fat emulsion, lactate (e.g., lactate salt and breast milk), and the like are also included. Examples of the serum include adult bovine serum, calf serum, neonatal calf serum, and fetal calf serum, etc. Examples of the basal medium include an RPMI medium, an MEM medium, a HamF-12 medium, a DM-160 medium and the like. In other words, the aqueous solution for cell preservation of the present invention refers to an aqueous solution which is free of any natural animal-derived component as exemplified above but contains synthetic chemicals alone or both chemicals and components derived from plants.

The aqueous solution for cell preservation of the present invention refers to a combination of a thickener, a cryoprotectant, and sugars. In addition, the solution may be further combined with a pH adjuster. Those components are used in the state of aqueous solution. However, any type of such a usage corresponds to the use of the present invention that powder, which is subjected to freeze drying or the like, is dissolved in water or the like and then used as an aqueous solution and that what is previously prepared in an aqueous state is directly used.

The thickener of the present invention may be any of thickeners as long as the thickener can constitute an aqueous solution for cell preservation capable of adequately preserving cells even in an aqueous solution entirely free of natural animal-derived component. Examples of the thickener include carboxymethylcellulose (hereinafter, referred to as CMC), carboxymethylcellulose-Na (hereinafter, referred to as CMC-Na), organic acid polymers, propylene glycol alginate, and sodium alginate and the like. Of those, CMC or CMC-Na is preferably used. In particular, CMC-Na is preferably used. Further, out of the organic acid polymers, sodium polyacrylate is preferably used. The content of the thickener in the aqueous solution for cell preservation is preferably 0.1 to 1.0 w/v %, more preferably 0.1 to 0.5 w/v %, particularly preferably 0.25 w/v %.

The cryoprotectant of the present invention may be any of cryoprotectants as long as the cryoprotectant can constitute an aqueous solution for cell preservation capable of adequately preserving cells even in an aqueous solution entirely free of any natural animal-derived component. Examples of the cryoprotectant include DMSO, glycerol, propylene glycol, and 1-methyl-2-pyrrolidone and the like. Of those, DMSO and propylene glycol are preferably used. In particular, DMSO is preferably used. The content of the cryoprotectant in the aqueous solution for cell preservation is preferably 5 w/v % or more but less than 15 w/v %, most preferably 5 to 12 w/v %. In the range, a content of 10 w/v % is particularly preferable.

The sugar of the present invention may be any of sugars as long as the sugar can constitute an aqueous solution for cell preservation capable of adequately preserving cells even in an aqueous solution entirely free of any natural animal-derived component. Examples of the sugar include glucose, trehalose, sucrose, and lactose and the like. Of those, glucose is particularly preferably used. The content of the sugars in the aqueous solution for cell preservation is preferably 1.0 to 10.0 w/v %, more preferably 3 to 5 w/v %, and in the range, a content of 3 w/v % is particularly preferable.

The pH adjuster of the present invention may be any of pH adjusters as long as the pH adjuster can constitute an aqueous solution for cell preservation capable of adequately preserving cells even in an aqueous solution entirely free of natural animal-derived component. Examples of the pH adjuster include sodium bicarbonate, HEPES, and a phosphate buffer, etc. In addition, when a basic stock solution (BSS) does not contain phosphate buffer, one added with sodium chloride, which has a function of imparting a buffer capacity around a pH value suitable for cells, can also be used. Of those, the phosphate buffer is particularly preferably used. The pH adjuster is preferably used in an appropriate amount for adjusting the pH of the aqueous solution for cell preservation to about 6.5 to 9.0, more preferably 7.0 to 8.5. By the way, the phosphate buffer of the present invention refers to, for example, sodium chloride, monosodium phosphate (anhydrous), monopotassium phosphate (anhydrous), disodium phosphate (anhydrous), trisodium phosphate (anhydrous), potassium chloride, or potassium dihydrogen phosphate (anhydrous), etc. In particular, sodium chloride, monosodium phosphate (anhydrous), potassium chloride, or potassium dihydrogen phosphate (anhydrous) is preferably used.

The content of the pH adjuster in the aqueous solution for cell preservation is preferably 0.01 to 1.0 w/v %, more preferably 0.05 to 0.5 w/v %.

The osmotic pressure of the aqueous solution for cell preservation of the present invention is preferably 1,000 mOsm or more, more preferably 1,000 to 2,700 mOsm to keep the performance of the solution as a preservation solution.

The composition of the aqueous solution for cell preservation of the present invention may be any combination of the specifically exemplified components listed above as long as cells can be adequately preserved. Examples of the composition include: an aqueous solution for cell preservation prepared by mixing appropriate amounts of CMC as a thickener, DMSO as a cryoprotectant, glucose as a sugar, sodium bicarbonate and HEPES as a pH adjuster; and an aqueous solution for cell preservation obtained by further adding a phosphate buffer to the above solution. In addition, the composition may include CMC-Na or an organic acid polymer instead of CMC as a thickener. Alternatively, the composition may include propylene glycol, etc. instead of DMSO as a cryoprotectant.

The aqueous solution for cell preservation of the present invention is desirably one having a survival rate of 80% or more, preferably 90% or more, more preferably 100% after preservation for at least 1 week, though the survival rate may vary depending on cells to be preserved.

A method for cell preservation of the present invention may be any of methods with which cells can be adequately preserved. For example, the method may involve: dispersing cells to be preserved in the aqueous solution for cell preservation of the present invention; dispensing the suspension into a container such as an ampule or a cryotube; preliminarily freezing the suspension for 20 to 30 minutes; and then subjecting the suspension to cryopreservation at −80° C. or −196° C. According to the preservation method of the present invention, cryopreservation can be performed without a program freezer.

The number of preserved cells in the aqueous solution for cell preservation is adjusted to, but not specifically limited to, preferably $1 \times 10^5$ to $\times 10^7$ cells/mL, more preferably $5 \times 10^5$ to $5 \times 10^6$ cells/mL.

Cells to be preserved may be any kind of cells as long as the cells can be preserved with the aqueous solution for cell preservation of the present invention. Examples of such cells include established cell lines, lymphocytes, spleen cells, thymocytes, fertilized eggs, myeloma cells, somatic stem cells, mesenchymal stem cells, and embryonic stem cells (ES cells), etc. of various animals. In particular, the animal may be mouse, (e.g., BALB/C, ICR, and C3H), rat, rabbit, guinea pig, cat, cow, goat, dog, pig, or human, etc. In addition, the aqueous solution for cell preservation of the present invention may be used for not only the preservation of cells but also the preservation of tissues and of organs.

Hereinafter, the present invention will be described in more detail with reference to examples. However, the present invention is not limited to these examples.

Example 1

<Preparation of Aqueous Solution for Cell Preservation>

1. Preparation of Each Component

The respective components of an aqueous solution for cell preservation were prepared as described below:

(1) Thickener a. CMC

CMC was prepared in a total volume of 750 mL by dissolving 5 g of carboxymethylcellulose (manufactured by Wako Pure Chemical Industries, Ltd.) in distilled water at high temperature or at normal temperature b. CMC-Na CMC-Na was prepared in a total volume of 750 mL by dissolving 5 g of sodium carboxymethylcellulose (manufactured by Wako Pure Chemical Industries, Ltd.) in distilled water at high temperature or at normal temperature.

c. Sodium Polyacrylate

Sodium polyacrylate was prepared in a total volume of 750 mL by dissolving 5 g of sodium polyacrylate (manufactured by Wako Pure Chemical Industries, Ltd.) in distilled water.

(2) Cryoprotectant d. Dimethyl Sulfoxide (DMSO)

One hundred mL of dimethyl sulfoxide (manufactured by Wako Pure Chemical Industries, Ltd.) was used.

e. Propylene Glycol

One hundred mL of propylene glycol (manufactured by Wako Pure Chemical Industries, Ltd.) was used.

(3) Sugars, pH Adjusters, etc.

f. Phosphate Buffer

A phosphate buffer (manufactured by Nissui Pharmaceutical Co., Ltd.) was used.

g. Basic Stock Solution (Hereinafter BSS)

BSS was prepared in a total volume of 150 mL by adding 30.0 g of glucose, 0.8 g of sodium bicarbonate, 0.36 g of HEPES (manufactured by Wako Pure Chemical Industries, Ltd.), and 1.576 g of PBS (manufactured by Nissui Pharmaceutical Co., Ltd.) to double-distilled water.

(4) Basal Medium (for Comparison)

h. RPMI1640

RPMI1640 (manufactured by Dainippon Pharmaceutical Co., Ltd.) was used in an amount of 1.576 g.

2. Preparation

The respective components prepared in the above item 1 were mixed while being stirred to prepare each composition as described in Table 1. The respective compositions were sterilized by filtering through a series of decreasing pore size of 1.0 μm, 0.5 μm, and 0.22 μm filter (manufactured by Millipore Co., Ltd.).

TABLE 1

| | | Aqueous solution for cell preservation (g/L) | | | | | | | | | | | | Comparison |
|---|---|---|---|---|---|---|---|---|---|---|---|---|---|---|
| | Component | A | B | C | D | E | F | G | H | I | J | K | L | M |
| Thickener | CMC | 5 | | | | | | 5 | | | | | | 5 |
| | CMC—Na | | | 5 | | | | | | 5 | | | | |
| | Organic acid polymer | | | | | 5 | | | | | | 5 | | |
| Cryoprotectant | DMSO | 100 | — | 100 | — | 100 | — | 100 | — | 100 | — | 100 | — | 100 |
| | Propylene glycol | — | 100 | — | 100 | — | 100 | — | 100 | — | 100 | — | 100 | — |
| Sugars, pH adjusters | Phosphate buffer | | | — | | | | | | 1.576 | | | | |
| | BSS Glucose | | | | | | | 30 | | | | | | 30 |
| | Sodium bicarbonate | | | | | | | 0.8 | | | | | | 0.8 |
| | HEPES | | | | | | | 0.36 | | | | | | 0.36 |
| Minimal essential medium | RPMI1640 | | | | | | | — | | | | | | 1.576 |
| Water | Distilled water | Adequate amount | | | | | | | | | | | | |

<Performance Test and Specification Test of Aqueous Solution for Cell Preservation>

1. Performance Test

The performance of an aqueous solution for cell preservation was investigated by measuring the survival rate of cells upon preservation.

X63Ag8-6.5.3 (mouse myeloma) cells pre-cultured in an RPMI1640 culture medium added with 10-v/v % FBS were collected by centrifugation and then added with 1 mL each of the aqueous solutions for cell preservation C, I, and M so that the cells were suspended in the solution at $5 \times 10^5$ to $5 \times 10^6$ cells/mL, followed by dispensing the suspension into 2-mL-volume cryotubes (manufactured by Nunc Co., Ltd.). Immediately after that, the cryotubes were rapid-frozen at −80° C. and then preserved for 7 days (n=3).

2. Specification Test

The pH and osmotic pressure of each of the aqueous solutions for cell preservation prepared as described above were investigated.

In addition, the results of the performance test and the specification test for the respective aqueous solutions for cell preservation were shown in Table 2 (n=3). As shown in Table 2, both of the aqueous preservation solution C and I showed a survival rate of 80% or more.

Consequently, the results confirmed that both of the aqueous preservation solutions C and I shown in Table 1 have preservation performance comparable to that of the aqueous preservation solution M containing a basal medium component despite that none of the solutions C and I contained the serum and the components of the basal medium.

TABLE 2

| Aqueous preservation solution | | C | | | I | | | M | |
|---|---|---|---|---|---|---|---|---|---|
| Performance test | Survival rate (%) | 90.5 | 90.1 | 88.8 | 95.1 | 92.7 | 95.3 | 97.2 | 98.2 | 95.7 |
| | Average (%) | | 89.8 | | | 94.4 | | | 97.0 | |
| Specification test | pH | | 7.89 | | | 7.86 | | | 7.98 | |
| | Osmotic (mOsm) pressure | | 2062 | | | 2107 | | | 2131 | |

Example 2

<Survival Rate of Different Types of Cells>

Cells described in Table 3, which had been harvested and fractionated beforehand from an RPMI1640 culture medium added with 10-v/v % FBS, were collected by centrifugation and added with either 1 mL of the aqueous solution for cell preservation J or the comparative aqueous solution for cell preservation M so that the cells were suspended in the solution at $5 \times 10^5$ to $5 \times 10^6$ cells/mL, followed by dispensing the suspension into 2-mL-volume cryotubes (manufactured by Nunc Co., Ltd.). Immediately after that, the cryotubes were rapid-frozen at −80° C. and then preserved for a certain period of time. The survival rates of cells after the respective preservation periods in case of lymphocytes are shown in Table 3, the survival rates of cells after the respective preservation periods in case of spleen cells are shown in Table 4, and the survival rates of cells after the respective preservation periods in case of thymocytes are shown in Table 5.

TABLE 3

| <Lymphocytes> | Preservation period | Survival rate (%) | | | | | |
|---|---|---|---|---|---|---|---|
| Animal species | (days) | I | | | M | | |
| Cat | 7 | 98.6 | 100.0 | 97.1 | 100.0 | 100.0 | 100.0 |
| Cattle | | 97.6 | 93.6 | 99.9 | 97.9 | 96.4 | 100.0 |
| Goat | | 100.0 | 100.0 | 100.0 | 100.0 | 100.0 | 100.0 |
| Dog | | 100.0 | 100.0 | 100.0 | 100.0 | 100.0 | 100.0 |
| Pig | | 100.0 | 99.8 | 100.0 | 100.0 | 100.0 | 100.0 |
| Human being | | 97.0 | 99.4 | | 97.4 | 98.5 | |
| Cattle (2nd) | 7 | | 100.0 | | | 100.0 | |
| Time-dependent | 14 | | 100.0 | | | 100.0 | |
| stability test | 30 | | 100.0 | | | 100.0 | |
| | 60 | | 100.0 | | | 100.0 | |

TABLE 4

| <Spleen cells> | Preservation | Survival rate (%) | |
|---|---|---|---|
| Kinds of mice | period (days) | I | M |
| BALB/C(1 year) | 7 | 98.0 | 97.9 |
| BALB/C(6W) | | 96.1 | 98.4 |
| ICR(8W) | | 100.0 | 100.0 |
| C3H(7W) | | 100.0 | 100.0 |

TABLE 5

| <Thymocytes> | Preservation | Survival rate (%) | |
|---|---|---|---|
| Kinds of mice | period (days) | I | M |
| BALB/C(1 year) | 7 | 96.0 | 93.4 |
| BALB/C(6W) | | 93.6 | 98.3 |
| ICR(8W) | | 99.9 | 99.8 |
| C3H(7W) | | 99.9 | 99.7 |

As shown in Tables 3 to 5, a survival rate of nearly 100.0% was shown upon the preservation of each of lymphocytes, spleen cells, and thymocytes of various animal species with the aqueous solution for cell preservation of the present invention. The results confirmed that the aqueous solution for cell preservation of the present invention was capable of adequately preserving cells even in the absence of any natural animal-derived component.

Example 3

<Investigation of Concentration of Glucose>

Cell preservation solutions C and N to R were prepared using the respective components prepared in 1. of Example 1 described above so that their compositions described in Table 6 could be obtained. In addition, in a manner similar to Example 1 described above, the performance test and specification test of each aqueous solution for cell preservation were carried out, by using X63Ag8-6.5.3. cells. The results of the tests were shown in Table 6.

As shown in Table 6, the aqueous preservation solutions containing 2 w/v % or less or 7 w/v % of glucose each showed a low survival rate. In contrast, the aqueous preservation solutions each containing at least 3 to 5 w/v % of glucose each showed a survival rate of 80% or more.

Jurkat: human T-cell leukemia cells

Each of the cells was cultured in an RPMI1640 culture medium added with 10% fetal calf serum under the conditions of 5% $CO_2$ at 37° C.

TABLE 6

|  |  | Aqueous solution for cell preservation (g/L) | | | | | |
| --- | --- | --- | --- | --- | --- | --- | --- |
| Components | | N | O | C | P | Q | R |
| Thickener | CMC—Na | | | 5 | | | |
| Cryoprotectant | DMSO | | | 100 | | | |
| Sugars, | Phosphate buffer | | | 1.576 | | | |
| pH adjusters | BSS Glucose | 10 | 20 | 30 | 40 | 50 | 70 |
| | Sodium bicarbonate | | | 0.8 | | | |
| | HEPES | | | 0.36 | | | |
| Water | Distilled water | | | Adequate amount | | | |
| Performance test | Survival rate (%) | 15.0 | 18.0 | 95.0 | 93.0 | 82.0 | 20.0 |

Example 4

<Investigation of Concentration of Cryoprotectant>
Cell preservation solutions C and S to X were prepared using the respective components prepared in 1. of Example 1 described above so that their compositions described in Table 7 could be obtained. In addition, in a manner similar to Example 1 described above, the performance test and specification test of each aqueous solution for cell preservation were carried out by using SK-007 cells or Jurkat cells. The results of the tests were shown in Table 7.

As shown in Table 7, the aqueous preservation solutions each containing 3 w/v % or less of DMSO or 15 w/v % of DMSO as a cryoprotectant each showed a low survival rate for any of cells. In contrast, the aqueous preservation solutions each containing at least 5 to 12 w/v % of DMSO showed a survival rate of 80% or more.

<SK-007 Cells, Jurkat Cells>
SK-007: human myeloid leukemia cells (B-cell leukemia cells)

TABLE 7

|  |  | Aqueous solution for cell preservation (g/L) | | | | | | |
| --- | --- | --- | --- | --- | --- | --- | --- | --- |
| Component | | S | T | U | V | C | W | X |
| Thickener | CMC—Na | | | | 5 | | | |
| Cryoprotectant | DMSO | 30 | 50 | 70 | 90 | 100 | 120 | 150 |
| Sugars, | Phosphate buffer | | | | 1.576 | | | |
| pH adjusters | BSS Glucose | | | | 30 | | | |
| | Sodium bicarbonate | | | | 0.8 | | | |
| | HEPES | | | | 0.36 | | | |
| Water | Distilled water | | | | Adequate amount | | | |
| Performance test | Survival rate SK-007 cells | 15.0 | 80.0 | 82.0 | 85.0 | 95.0 | 91.0 | 63.0 |
| | (%) Jurkat cells | 26.0 | 86.0 | 90.0 | 84.0 | 95.0 | 88.0 | 58.0 |
| Specification test | pH | 7.64 | 7.65 | 7.73 | 7.78 | 7.74 | 7.77 | 7.8 |
| | Osmotic pressure (mOsm) | 740 | 1080 | 1523 | 1956 | 2274 | 2698 | 3564 |

Example 5

<Investigation of Concentration of Thickener>
Cell preservation solutions Y to AC were prepared using the respective components prepared in 1. of Example 1 described above so that their compositions described in Table 8 could be obtained. In addition, in a manner similar to Example 1 described above, the performance test and specification test of each aqueous solution for cell preservation were carried out by using SK-007 cells or Jurkat cells. The results of the tests were shown in Table 8.

As shown in Table 8, the aqueous preservation solutions containing 0.1 w/v % to 1.0 w/v % of an organic acid polymer as a thickener showed a survival rate of 90% or more for any of cells

TABLE 8

| | Component | Aqueous solution for cell preservation (g/L) | | | | |
| --- | --- | --- | --- | --- | --- | --- |
| | | Y | Z | AA | AB | AC |
| Thickener | Organic acid polymer | 1.0 | 2.5 | 5.0 | 7.5 | 10.0 |
| Cryoprotectant | DMSO | | | 100 | | |
| Sugars, | Phosphate buffer | | | 1.576 | | |
| pH adjusters | BSS Glucose | | | 30 | | |
| | Sodium bicarbonate | | | 0.8 | | |
| | HEPES | | | 0.36 | | |
| Water | Distilled water | | | Adequate amount | | |
| Performance test | Survival rate SK-007 cells | 97.0 | 100.0 | 99.0 | 98.0 | 98.0 |
| | (%) Jurkat cells | 94.0 | 99.0 | 97.0 | 96.0 | 95.0 |
| Specification test | pH | 7.97 | 7.99 | 8.02 | 8.1 | 8.08 |
| | Osmotic pressure (mOsm) | 2098 | 2119 | 2124 | 2123 | 2172 |

Example 6

<Performance Test of Aqueous Solution for Cell Preservation>

The performance of an aqueous solution for cell preservation was evaluated by investigating the survival rate, proliferation ability, and differentiation ability of cells upon preservation.

1. Investigation of Survival Rate of Cells

The performance of each of the aqueous solutions for cell preservation M, I, and K was evaluated with respect to the survival rate of cells upon preservation. Human umbilical blood-derived mesenchymal stem cells cultured in advance in an IMDM culture medium supplemented with 10 v/v % FBS under the conditions of 5% $CO_2$ at 37° C. were added with 1 mL each of the aqueous solutions for cell preservation M, I, and K so that the cells were suspended in the solution at $2 \times 10^5$ cells/mL, followed by dispensing the resultant into 2-mL-volume cryotubes (manufactured by Nunc Co., Ltd.). Immediately after that, the cryotubes were rapid-frozen at −80° C., preserved for 4 days, and then preserved at −196° C. (liquid nitrogen tank) for 72 days (n=3).

Figure 1A:
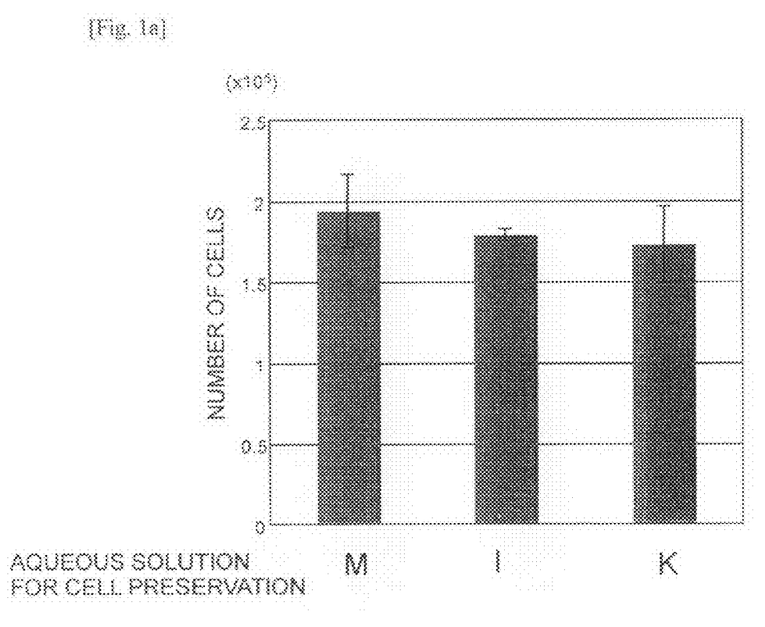
FIG. 1a is a diagram illustrating the numbers of surviving cells preserved in each of aqueous solutions for cell preservation M, I, and K (Example 6).

Frozen tubes containing cells were thawed at 37° C. in a waterbath, washed twice with mixture of 9 mL of IMDM and 1 mL of FBS. Cells were collected by centrifugation and the number of cells was counted. As represented in FIG. 1a, the aqueous solution for cell preservation I and K each showed similar survival rate of cells as that in the case of preservation in the aqueous solution for cell preservation M. The survival rates of cells in the respective aqueous solutions for cell preservation were 97% for M, 90% for I, and 86% for K, and each of them showed high performance in cell preservation.

2. Investigation of Proliferation Ability

Figure 1B:
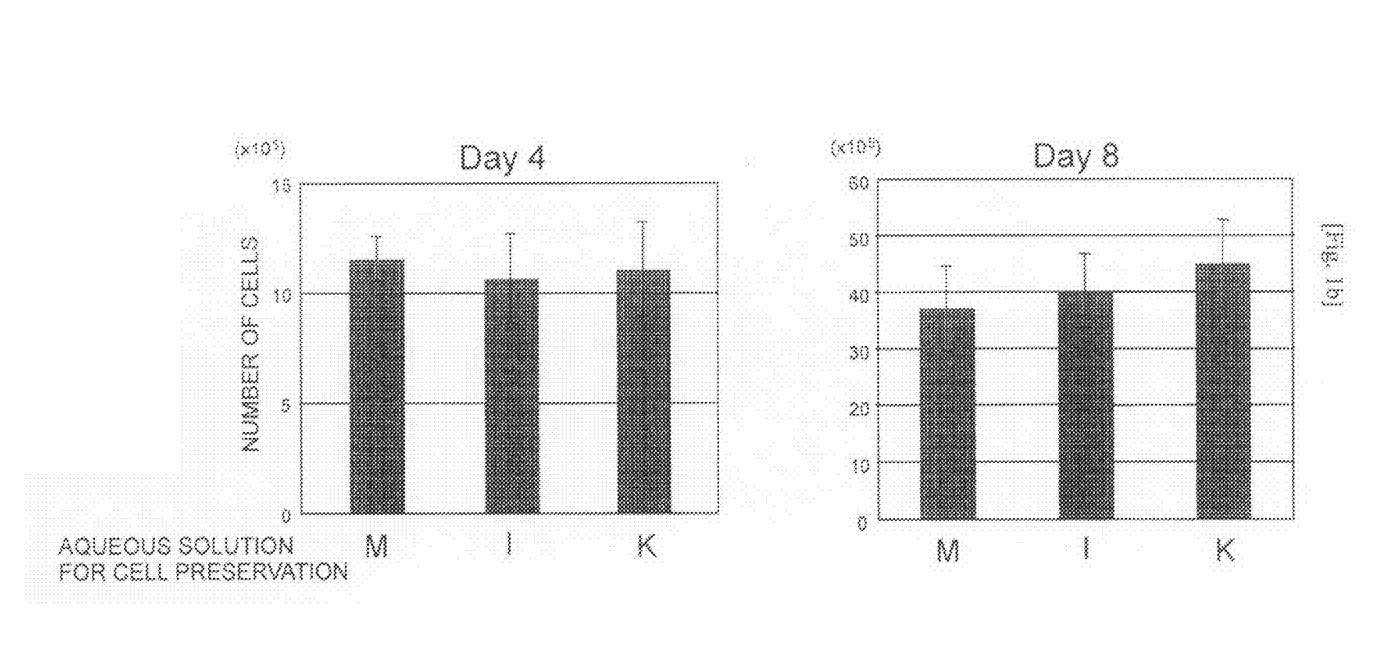
FIG. 1b is a diagram illustrating the number of proliferating cells preserved in each of the aqueous solutions for cell preservation M, I, and K (Example 6).

Retention of cell proliferation ability was investigated upon cells cryopreserved with preservation solution M, I, and K. The cells preserved in the above item 1. were seeded on a culture dish (35 mm) so that the number of cells be $5 \times 10^4$ cells and then cultured, followed by counting the numbers of cells after 4 days and 8 days. For the counting of cells, Trypan blue was used to exclude dead cells. As illustrated in FIG. 1b, cells preserved in each of the aqueous solutions for cell preservation I and K showed the similar cell growth as that of the cells preserved in the aqueous solution for cell preservation M. Therefore, the results confirmed that each of the aqueous solutions for cell preservation M, I, and K was capable of preserving cells while retaining the cell proliferation ability.

3. Investigation of Differentiation Ability

Cells preserved as described in the above item 1. were seeded on a culture dish (35 mm) so that the number of cells could be $5 \times 10^4$ cells and then cultured in an differentiation induction medium for osteoblast or adipocyte shown in Table 9 for 28 days, followed by investigating whether the cells each retained its differentiation ability.

TABLE 9

| | Differentiation induction medium for osteoblast | Differentiation induction medium for adipocyte |
| --- | --- | --- |
| Medium components | I MDM + 1 v/v % FBS<br>0.1 µM dexamethasone<br>50 µg/mL ascorbic acid<br>10 mM β-glycerol phosphate<br>10 ng/mL hEGF | I MDM + 10 v/v % FBS<br>0.1 µM dexamethasone<br>0.5 mM 3-isobutyl-1-methylxanthine<br>0.1 mM indomethacin |

Figure 2A:
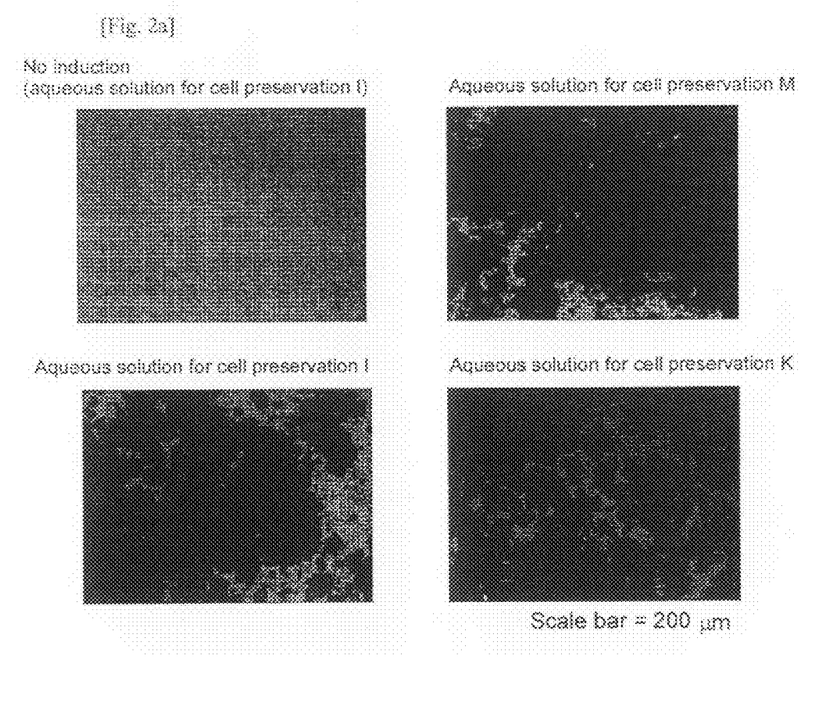
FIG. 2a is a diagram illustrating the differentiation of cells preserved in each of the aqueous solutions for cell preservation M, I, and K to osteoblast cells (Example 6).
Figure 2B:
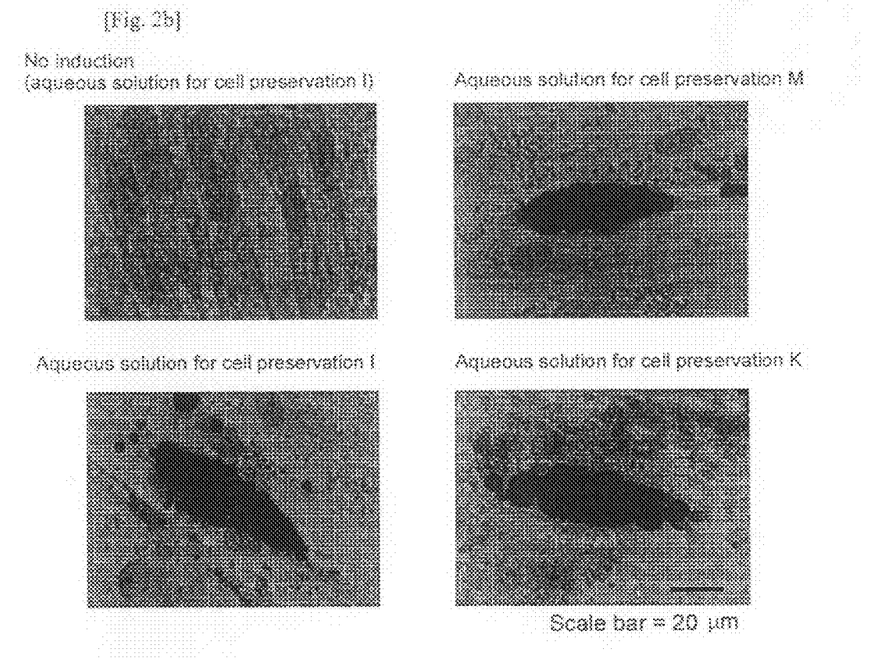
FIG. 2b is a diagram illustrating the differentiation of cells preserved in each of the aqueous solutions for cell preservation M, I, and K to adipocytes (Example 6).

As shown in FIG. 2a, Alizarin Red staining was performed 28 days after the culture. As a result, cells preserved in any of the aqueous solutions for cell preservation M, I, and K showed the induction of osteoblast differentiation. In FIG. 2b, likewise, oil-red O staining showed that the induction of adipocyte differentiation occurred in any of cells preserved in the aqueous solutions for cell preservation M, I, and K. Therefore, it was confirmed that each of the aqueous solutions for cell preservation M, I, and K was capable of preserving cells while retaining the differentiation ability of cells.

INDUSTRIAL APPLICABILITY

Since the cell preservation solution of present invention is free of natural animal-derived components from basal medium and serum, it consequently can be safe for medical use because of the low risk of contamination with impurities that may have influences on the cells to be preserved. Further, the solution is available at a low cost because the solution does not use any of a basal medium, serum, etc.

The invention claimed is:

1. An aqueous solution for cell preservation comprising (a) to (e) and having a pH of 6.5 to 9.0:
   (a) 1.0 to 20.0 w/v % of a cryoprotectant;
   (b) 1.0 to 10.0 w/v % of a sugar;

(c) 0.1 to 1.0 w/v % of a thickener;
(d) 0.01 to 1.0 w/v % of a pH adjustor; and
(e) a proper amount of water,
wherein the aqueous solution for cell preservation is free of natural animal-derived components.

2. An aqueous solution for cell preservation according to claim 1, further comprising a pH adjuster.

3. An aqueous solution for cell preservation according to claim 1 or 2, wherein the natural animal-derived components comprise serum and a basal medium.

4. An aqueous solution for cell preservation according to claim 1, wherein the aqueous solution for cell preservation of claim 1 has an osmotic pressure of 1,000 mOsm or more.

5. An aqueous solution for cell preservation according to claim 4, wherein the aqueous solution for cell preservation of claim 4 has an osmotic pressure of 1,000 to 2700 mOsm.

6. An aqueous solution for cell preservation according to claim 1, wherein the thickener comprises carboxymethylcellulose (CMC), sodium carboxymethylcellulose (CMC-Na), or an organic acid polymer.

7. An aqueous solution for cell preservation according to claim 6, wherein the organic acid polymer, comprises sodium polyacrylate.

8. An aqueous solution for cell preservation according to claim 1, wherein the cryoprotectant comprises dimethyl sulfoxide (DMSO) or propylene glycol.

9. An aqueous solution for cell preservation according to claim 1, wherein the sugar comprises glucose.

10. An aqueous solution for cell preservation according to claim 1, wherein the pH adjuster comprises a phosphate buffer.

11. An aqueous solution for cell preservation, comprising the following compositions (a) to (e) and having a pH of 6.5 to 9.0:
(a) 5.0 to 12.0 w/v % of DMSO;
(b) 3.0 to 5.0 w/v % of glucose;
(c) 0.2 to 0.7 w/v % of a thickener;
(d) 0.01 to 1.0 w/v % of a phosphate buffer; and
(e) a proper amount of water,
wherein the aqueous solution for cell preservation is free of natural animal-derived components.

12. An aqueous solution for cell preservation according to claim 1, wherein cells to be preserved comprise any of lymphocytes, spleen cells, thymocytes, animal cells, somatic stem cells, mesenchymal stem cells, and embryonic stem cells.

13. An aqueous solution for cell preservation according to claim 1, wherein the aqueous solution is used for medical applications.

14. An aqueous solution for cell preservation according to claim 1, wherein a method for cell preservation comprises cryopreservation.

15. An aqueous solution for cell preservation according to claim 1, wherein a survival rate of cells after preservation is at least 80%.

16. An aqueous solution for cell preservation according to claim 1, wherein a proliferation ability of cells is retained after preservation for 4 days at −80° C. or after preservation for 72 days at −196° C.

17. At aqueous solution for cell preservation according to claim 1, wherein a differentiation ability of cell after preservation is retained.

18. A method for cell preservation, comprising: dispersing cells in the aqueous solution for cell preservation according to claim 1; dispensing the cells into containers; and subjecting the cells to cryopreservation.

19. A method for cell preservation according to claim 18, wherein the number of the dispensed cells is $1\times10^5$ to $1\times10^7$ cells/mL.

20. An aqueous solution for cell preservation according to claim 1 or claim 11, wherein the aqueous solution is free from origin undefined amino acids.

* * * * *

UNITED STATES PATENT AND TRADEMARK OFFICE
CERTIFICATE OF CORRECTION

PATENT NO. : 8,460,926 B2
APPLICATION NO. : 12/084655
DATED : June 11, 2013
INVENTOR(S) : Yamashiro et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1285 days.

Signed and Sealed this
Eighth Day of September, 2015

Michelle K. Lee
*Director of the United States Patent and Trademark Office*